(12) United States Patent
Anitua Aldecoa

(10) Patent No.: US 9,861,684 B2
(45) Date of Patent: Jan. 9, 2018

(54) FORMULATION OF A BLOOD COMPOSITION THAT IS RICH IN PLATELET AND/OR GROWTH FACTORS AND CONTAINS GELLED PROTEINS, AND A METHOD FOR ITS PREPARATION

(71) Applicant: BIOTECHNOLOGY INSTITUTE, I MAS D, S.L., Vitoria (Alava) (ES)

(72) Inventor: Eduardo Anitua Aldecoa, Vitoria (ES)

(73) Assignee: BIOTECHNOLOGY INSTITUTE, I MAS D, S.L., Vitoria (Alava) (ES)

( * ) Notice: Subject to any disclaimer, the term of this patent is extended or adjusted under 35 U.S.C. 154(b) by 729 days.

(21) Appl. No.: 14/447,853

(22) Filed: Jul. 31, 2014

(65) Prior Publication Data
US 2015/0037430 A1    Feb. 5, 2015

(30) Foreign Application Priority Data
Aug. 1, 2013 (ES) .................................. 201300718

(51) Int. Cl.
| A61K 38/36 | (2006.01) |
| A61K 35/16 | (2015.01) |
| A61K 35/19 | (2015.01) |
| A61K 45/06 | (2006.01) |
| A61K 35/14 | (2015.01) |

(52) U.S. Cl.
CPC .............. *A61K 38/36* (2013.01); *A61K 35/14* (2013.01); *A61K 35/16* (2013.01); *A61K 35/19* (2013.01); *A61K 45/06* (2013.01)

(58) Field of Classification Search
CPC .................................................... A61K 36/00
USPC ....................................................... 424/725
See application file for complete search history.

(56) References Cited

U.S. PATENT DOCUMENTS

| 2008/0281081 A1 | 11/2008 | Shanbrom |
| 2013/0030161 A1 | 1/2013 | Anitua |

FOREIGN PATENT DOCUMENTS

| ES | 2333498 A1 | 2/2010 |
| ES | 2369945 A1 | 12/2011 |
| WO | 0067774 A2 | 11/2000 |
| WO | 2008011192 A2 | 1/2008 |
| WO | 2009016451 A2 | 2/2009 |
| WO | 2010142784 A2 | 12/2010 |
| WO | 2011150328 A1 | 12/2011 |

OTHER PUBLICATIONS

Anitua, E. et al. "Perspectives and challenges in regenerative medicine using plasma rich in growth factors". Journal of Controlled Release. 157 (1) 29-38 (Jun. 6, 2011).
Rai et al "An in vitro evaluation of PCL-TCP composites as delivery systems for platelet-rich plasma" Journal of Controlled Release. 330-342 : 107 (2005).
Nunez et al "Effectiveness of Heated Hematic Derivatives (Autologous Serum & Plasma Rich in Growth Factors) in Corneal Epithelial Wound Healing" 2011 (May 2011).
Anitua et al "Perspectives and challenges in regenerative medicine using plasma rich in growth factors" Journal of Controlled Release. 157 : 29-38 (2012).
Aghaie et al "Preparation of albumin from human plasma by heat denaturation method in plasma bag" Official Journal of the British Blood transfusion Society. (2012).
Spanish priority application search report, dated Feb. 27, 2015, from corresponding application No. 201300718.
International Search report, dated Oct. 22, 2014, from corresponding application No. ES2014070623.

*Primary Examiner* — Michael V Meller
(74) *Attorney, Agent, or Firm* — Browdy and Neimark, PLLC

(57) ABSTRACT

Formulation comprising, or derived from, an initial blood composition, wherein the formulation is rich in platelets and/or growth factors and proteins originating from the initial blood composition, and wherein the proteins are in a gelled state. The invention also refers to method for preparing the formulation, comprising the steps of heating and then cooling the initial blood composition at certain temperatures and times. Among other advantages, the formulation in accordance with the invention is biocompatible and biodegradable, presents the desirable biological or medical properties provided by the presence of platelets or growth factors, and also presents high dimensional stability over time.

7 Claims, 11 Drawing Sheets

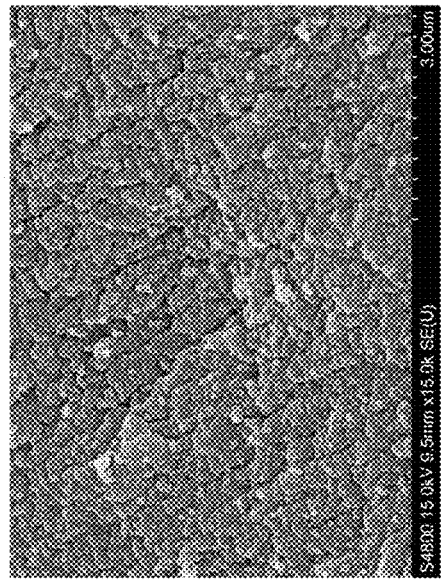
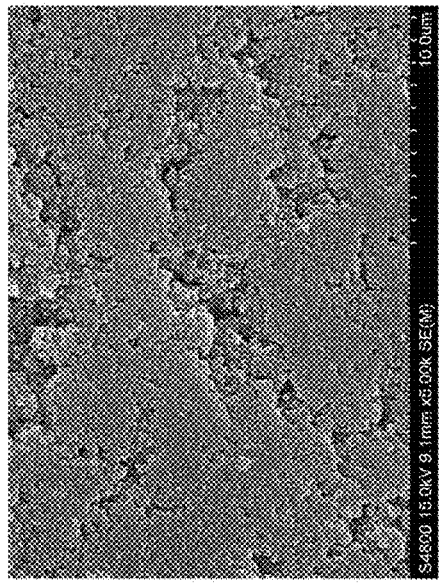
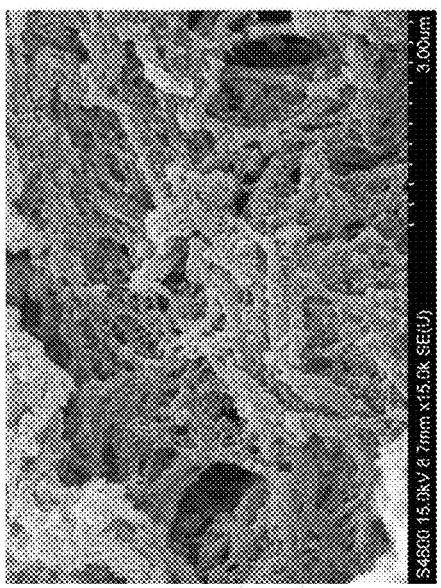
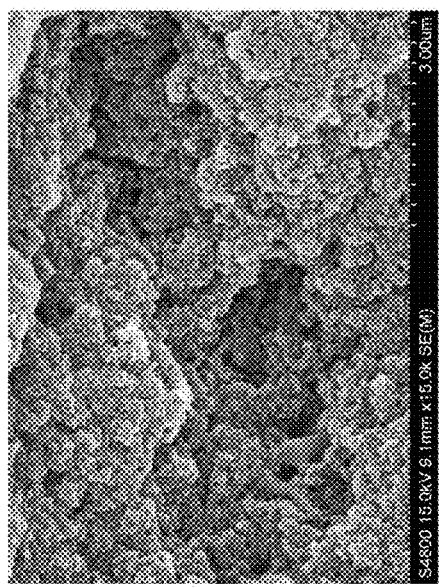
FIG.1
FIG.2

FORMULATION OF A BLOOD COMPOSITION THAT IS RICH IN PLATELET AND/OR GROWTH FACTORS AND CONTAINS GELLED PROTEINS, AND A METHOD FOR ITS PREPARATION

TECHNICAL FIELD

The invention relates to a formulation with desirable biological or medical properties, obtained from an initial platelet-rich and/or growth-factor-rich blood composition. The invention also relates to a method for preparing said formulation.

PRIOR ART

Prior art has described the preparation of compositions from human or animal blood, where the blood is processed in such a way that a platelet-rich plasma (PRP) and/or a growth-factor-rich plasma (PRGF) presenting useful biological and medical properties is/are obtained. Said PRP or PRGF have been used successfully in ex vivo applications, for example as a cell culture medium, and in vivo, for example to carry out a bone regeneration process in a patient or to treat a patient suffering from joint pain by means of infiltrations. In the event that said compositions are to be used in in vivo applications to treat a patient, the technology for preparing PRP and PRGF formulations has developed towards the preparation of autologous compositions, i.e. compositions obtained from the blood of the patient him/herself. Examples of these types of compositions and preparation methods may be found in patents U.S. Pat. No. 6,569,204 and ES2221770.

In the last few years technology has also been evolving with the objective of ensuring that compositions rich in platelets and/or growth factors can be obtained in the form of galenic compositions or pharmaceutical formulations. A galenic composition or pharmaceutical formulation is understood as the individualised provision to which medicines or main active substances, whether of chemical or biological origin (as is the case with the proteins in PRP or PRGF), are adapted in order to facilitate their administration. The galenic composition or pharmaceutical formulation of a medicine is of central importance as it determines the effectiveness and safety of the medicine, since it controls the dosage and the passage of the molecules of the medicine to the tissue. Furthermore, the galenic composition or pharmaceutical formulation of the medicine is a determining factor in ensuring that the preparation of the medicine, its dosage and its administration are known, controlled and capable of being executed with relative ease and in a repeatable manner. In short, a galenic composition or pharmaceutical formulation seeks to facilitate the handling, conservation, transport, administration and, as a whole, the properties of any medicine or substance used for a therapeutic purpose.

One of the most widely applied medical formulations of PRP or PRGF is known as fibrin gel or fibrin mesh, which is a formulation with a semi-solid consistency that is very useful in certain applications. The procedure for the preparation of fibrin gel or mesh generally begins with a first phase in which the PRP or PRGF is obtained by an applicable method, for example by centrifuging blood extracted from a patient until the blood separates into various fractions, and extracting the top fraction, i.e. the fraction of platelet-rich plasma (PRP) or plasma rich in growth factors (PRGF). Then, the platelets contained in the PRP or PRGF are activated (activation being understood as the action of causing the platelets to release certain growth factors contained in their interior), for example by adding calcium chloride. As a result of the activation, and provided that a sufficient amount of time is allowed to pass, the polymerisation of fibrin from the fibrinogen contained in the plasma eventually takes place, thereby producing a final compound consisting in a fibrin clot (which is also known as fibrin gel or mesh because of its semi-solid consistency, resembling a type of biological sponge). This is the process that is usually performed in order to obtain a fibrin gel from blood modified with an anticoagulant, such as with sodium citrate. The blood may also be processed without it being mixed previously with anticoagulant. In this case, when the blood is centrifuged the plasma is separated from the red blood cells and the fibrin gel is obtained without the need for adding calcium chloride or any other platelet-activating agent. Fibrin gel or mesh can be used, for instance, in the following applications: to form a biological scaffold to fill bone defects; to be applied on wounds or injuries for the gradual release of growth factors; to be used as a matrix for the cultivation of stem cells; to be used as a membrane for sealing defects or ulcers; and its use in the manufacture of tissue, what is known as tissue engineering, where in addition to cells and growth factors it is especially important to have a matrix or scaffold on which the cells may grow.

Fibrin gel or mesh has some significant limitations. The main limitation of fibrin gel or mesh is the fact that it is unstable and tends to retract. As a result, fibrin gel or mesh is not capable of maintaining a stable volume over time or of providing a stable tissue support over time. Although this tendency to retract may be desirable in some applications, it is undesirable in others. For example, in a dental surgery technique known as sinus floor elevation, the biomaterial that is used to regenerate the bone defect must have osteoconductive properties but it must also be capable of maintaining the physical space for a long period of time until the bone matrix forms; otherwise, the space would collapse, adversely impacting the vertical regeneration of alveolar bone. Another example is the case of a breast removal (mastectomy), during which the biomaterial or gel that is used to fill the breast space must offer suitable mechanical resistance and provide a space and volume over a long period of time to ensure that said space does not collapse. A further example is the case of fillers or cosmetic filling agents (for example, hyaluronic acid), which are filling materials (providing and maintaining volume) widely used in the field of aesthetics to increase volume in corners and wrinkles and rectify said defects, providing a younger appearance; any agent that is designed to operate as a filler or filling agent must be mechanically stable and resistant to compression so that it is able to maintain the volume of the tissue. Furthermore, the tendency of fibrin gel or mesh to retract hampers and even prevents the use of the gel or mesh as an agent for releasing further external agents, medicines, proteins etc.

A further limitation of fibrin gel or mesh is its inability to be infiltrated or cannulated in its normal, semi-solid state, which prevents it from being administered as filler on the skin, in dermo-cosmetics, traumatology and in other fields such as biology or medicine.

It is the objective of this invention to provide a formulation having desirable biological or medical properties, obtained from an initial blood composition that is rich in platelets and/or growth factors, and which does not tend to retract, therefore allowing a stable volume to be maintained over time. Among other applications, it is desirable that the formulation provides an alternative to fibrin gel or mesh in certain applications where a stable composition is required.

BRIEF DESCRIPTION OF THE INVENTION

The invention pertains to a formulation with desirable biological or medical properties, comprising or deriving from an initial blood composition (of human or animal origin; autologous, homologous or heterologous), rich in platelets and/or growth factors, and which comprises proteins originating from the initial blood composition. The formulation presents the unique feature that said proteins are in a gelled state as a result of a thermal heating and cooling treatment. Specifically, gelled proteins are preferably albumin, glycoproteins, globulins and/or fibrinogen. The formulation of the present invention could be described as a "protein gel" (using terminology similar to that used to refer to fibrin gel) as it presents a gel-like consistency provided by the proteins in a gelled state. The formulation is deformable. The composition presents a new morphological and biomechanical configuration in comparison to other filling gels, other blood compositions rich in platelets and/or growth factors, and other similar compositions known in the prior art.

A method is also proposed for preparing the aforementioned formulation, the method comprising the steps of: obtaining an initial blood composition rich in platelets and/or growth factors, the basic formulation of which may vary; heating the initial blood composition at a temperature between 60° C. and 100° C. for at least one minute; cooling the initial blood composition for at least one minute. This inventive method, which may be regarded as a thermal sequence, provides volume and rigidity to a blood composition rich in platelets and/or growth factors, producing a protein gel or formulation with the consistency of gel thanks to the gelled state of certain proteins comprised in the initial blood composition.

The formulation of the present invention is biocompatible, biodegradable and presents the desirable biological or medical properties provided by the presence of platelets or growth factors. In addition, it also has a dense or viscous consistency due to the gelled state of certain proteins contained in the initial blood composition, said dense or viscous consistency being stable over time. The formulation of the present invention is therefore an advantageous alternative to fibrin gel or mesh, due to the fact that the formulation does not retract and thus allows a physical space to remain filled. In addition, the formulation provides good resistance to compression, similarly to or better than hyaluronic acid (commonly used as a filler or filling agent), and satisfactorily withstands the resistance that a tissue may exert. As a result, the formulation is highly suitable for use as a filler or filling agent. Furthermore, even when both the fibrin mesh and the inventive formulation are semi-solid in nature, only the latter may be infiltrated or injected due to the fact that it is deformable. An additional advantage of the formulation is that it can be dried and later rehydrated.

BRIEF DESCRIPTION OF THE DRAWINGS

Details of the invention can be seen in the accompanying non-limiting drawings:

FIG. 1 shows two electron microscopic images of an exemplary formulation in accordance with the invention.

FIG. 2 shows two electron microscopic images of another exemplary formulation in accordance with the invention.

DETAILED DESCRIPTION OF THE INVENTION

Figure 3:
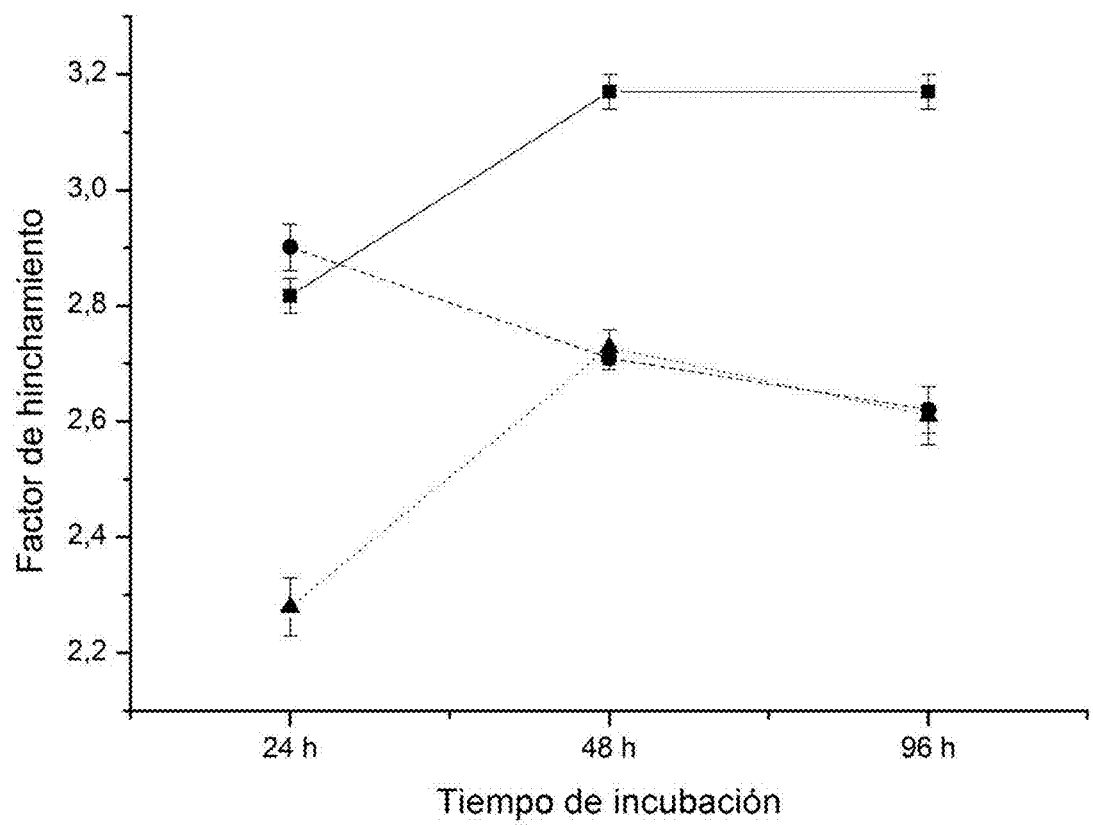
FIG. 3 shows the swelling factor of various formulations as per the invention, prepared from a fibrin clot treated at different temperatures and times.

In order to overcome existing problems in the prior art related to the lack of stability of fibrin gels and meshes, an alternative formulation with desirable biological or medical properties and with enhanced stability over time is proposed. The formulation comprises or is derived from an initial blood composition. The blood composition is rich in platelets and/or growth factors and also comprises various proteins. Therefore, the formulation is also rich in platelets and/or growth factors and comprises various proteins. Among said proteins, there are certain proteins in a gelled state, which means to say that they are denaturalised, and forming an organised protein network, preferably due to a thermal heating and cooling treatment. The proteins in a gelled state are preferably albumin, glycoproteins, globulins and/or fibrinogen. It has been proven that the protein gel in accordance with the present invention does not retract, can easily be cannulated or infiltrated, and maintains volume and space, unlike other gels based on a fibrin network only.

The initial blood composition may, for example, be a platelet-rich blood plasma, i.e. plasma with a high concentration of platelets. Said plasma is generally obtained by means of a blood centrifugation technique (in order to separate blood into a fraction of red blood cells, a fraction of white blood cells and a fraction of platelet-rich plasma (PRP)) followed by a step of separating all or part of the fraction of platelet-rich plasma (PRP).

The initial blood composition may also be a supernatant of a platelet-rich blood plasma (PRP). The supernatant is a substantial liquid that appears on the clot when the coagulation of a platelet-rich plasma (PRP) and its subsequent retraction is caused.

The initial blood composition may be a blood plasma rich in released growth factors (PRGF), i.e. a platelet-rich blood plasma that has been activated (for example, by adding calcium chloride, thrombin, a combination of calcium chloride and thrombin, sodium gluconate, collagen, or of any other agent that acts by activating the platelets and inducing the formation of fibrin) with the result that the platelets release certain growth factors in their interior.

Similarly, the initial blood composition may be a supernatant of a blood plasma rich in released growth factors (PRGF), i.e. a supernatant obtained following a coagulation and subsequent retraction of a platelet-rich plasma that has been previously activated (for example, by adding calcium chloride, thrombin, a combination of calcium chloride and thrombin, sodium gluconate, collagen, or of any other agent that acts by activating the platelets and inducing the formation of fibrin). Activation causes the platelets to release certain growth factors in their interior.

The initial blood composition may or may not contain leukocytes.

The initial composition may also be a fibrin gel obtained directly from processing blood that has not been modified with an anticoagulant.

A method for preparing a formulation with desirable biological or medical properties is also proposed, where said method comprises the steps of:
 a) being provided with an initial blood composition that is rich in platelets and/or growth factors, which is preferably a platelet-rich plasma with or without leukocytes, a plasma rich in growth factors with or without leukocytes, a supernatant of a platelet-rich plasma with or without leukocytes, a supernatant of a plasma rich in growth factors with or without leukocytes, or a fibrin gel obtained from blood that has not been modified with anti-coagulant;
 b) in the event that the blood composition has platelets, optionally activating the platelets with an activating agent such as calcium chloride, thrombin, calcium gluconate, collagen or any other activating agent, or a combination thereof, and waiting until a provisional fibrin is formed;
 c) heating the initial blood composition at a temperature of between 60° C. and 100° C. for at least one minute;
 d) cooling or tempering the initial blood composition for at least one minute.

The aforementioned method develops a thermal shock on the initial blood composition with the result of inducing a protein gelation of several proteins in the human plasma; among those proteins are albumin, glycoproteins, globulins and/or fibrinogen. For the purposes of this invention, "gelation" is the name given to the process that the molecules undergo and in which they polymerise or join together to form an organised protein network. In summary, as a result of the thermal shock process, new biocompatible and biodegradable formulations are created, depending on the initial blood composition, the common denominator of which is gelation or protein polymerisation.

In addition, it has been shown that the formulation in accordance with the invention, provided with gelled proteins, largely maintains the levels of growth factors in the initial blood composition. In other words, the thermal shock does not cause the mass destruction of growth factors in said initial blood composition.

Preferably, the initial blood composition is heated at a temperature of between 70° C. and 85° C.

The initial blood composition, which is rich in platelets and/or growth factors, is of human or animal origin. It may also be autologous (belonging to a patient to be treated at a later stage with the final formulation), homologous (belonging to a member of the same species as the patient, patients, cells or another biological entity to be treated or processed with the final formulation) or heterologous (belonging to a member of a different species to the patient, patients, cells or another biological entity to be treated or processed with the final formulation).

The invention contemplates that the initial blood composition may optionally include one or more additional substances, added prior to the claimed heat treatment. Said additional substances may be:
 one or more bioactive agents selected from proteins, peptides, nucleic acids, polysaccharides, lipids, non-protein organic substances and inorganic substances;
 one or more biodegradable polymers selected from: hyaluronic acid, hyaluronate salts, chondroitin 4-sulphate, chondroitin 6-sulphate, dextran, silica gel, alginate, hydroxypropyl methylcellulose, chitin derivatives—preferably chitosan—, xanthan gum, agarose, polyethylene glycol (PEG), polyhydroxyethyl methacrylate (PHEMA) synthetic or natural proteins and collagens;
 one or more organic polymers selected from the group formed by polycaprolactone, polyglycolide, polylactide and their copolymers;
 one or more of the following agents: antibiotics, antimicrobials, anticarcinogens, analgesics, growth factors, hormones;
 one or more inorganic components selected from the group of calcium salts, magnesium salts and/or strontium salts.

The invention also contemplates that any of the aforementioned substances may be added to the formulation after the heat treatment is carried out.

The formulation in accordance with the invention may present a variety of embodiments in which, in addition to the technical aspects claimed, the formulation can comprise further compounds, components and molecules etc that are suitable for the specific application for which the formulation will be used. I.e., the invention is regarded as a family of new formulations based on protein gels, said family being formed by different formulations in which gelled proteins are present and which may differ in their additional composition.

Furthermore, additional steps may be carried out on the formulation with gelled proteins, including drying matrices as a means of making them more versatile. In other words, the formulations of inventive gelled proteins may be dried (dry heat) or lyophilised in order to form a membrane. This membrane may subsequently be rehydrated by means of a variety of alternatives such as adding a saline solution, a platelet-rich plasma, a supernatant of a platelet-rich plasma, a plasma rich in growth factors, a supernatant of a plasma rich in growth factors, or any other solution that allows the membrane to be hydrated.

EXAMPLES

Example 1

The method starts with a 9 ml sample of blood extracted from a patient and stored in a hermetically sealed tube not containing citrate anticoagulant. The blood is centrifuged at a speed of 580 g for 8 minutes and at an ambient temperature. As a result of the centrifuging, the blood contained in the tube is divided into various fractions. The top fraction, or fraction of platelet-rich plasma (PRP), which includes the white blood cells, is extracted to a 5 ml syringe. Because the initial tube was not citrated, the PRP starts to coagulate. The contents of the syringe are heated at a temperature of 70° C. for 10 minutes. The container is then cooled at a temperature of 4° C. for 2 minutes. As a result of this thermal heating-cooling sequence, a semi-solid substance with the consistency of gel is formed inside the syringe. An activated formulation is thus obtained, the activated formulation presenting a gel-like consistency (both as a result of the fibrin generated due to the coagulation and as a result of the gelation of the proteins produced by the heat treatment) and lacking citrate and calcium. The presence of fibrin provides the formulation with greater consistency and resistance, while the gelled proteins provide constant stability and volume. Thanks to its properties and mechanical resistance, a substance of this type can be useful, for example, in correcting vertical defects in facial tissues.

Example 2

The method starts with a 9 ml sample of blood extracted from a patient and stored in a tight-sealed extraction tube that contains 3.8% citrate anticoagulant in an amount of 0.1 ml. The blood is centrifuged at a speed of 580 g for 8 minutes and at an ambient temperature. As a result of the centrifuging, the blood contained in the tube is divided into various fractions. The top fraction, or fraction of platelet-rich plasma (PRP), is extracted to a 5 ml syringe without including the white cells. The syringe is heated at a temperature of 80° C. for 3 minutes. The syringe is then cooled at a temperature of 20° C. for 10 minutes. As a result of this thermal heating-cooling sequence, a semi-solid substance is formed inside the second container. The substance has a gel-like consistency, and its platelets have yet to be activated. The substance does not comprise fibrin because it has not coagulated beforehand. A substance of this type may be used, for example, as a filler in cosmetic surgery, in order to achieve a more youthful look by eliminating or reducing the presence of wrinkles; the substance can be used thanks to its ability to be injected (using a needle smaller than or equal to 25 G) and to its consistency, which is capable of lifting skin. This bio-gel is stable over time and also releases growth factors that stimulate cell growth and proliferation, which make it very advantageous therefore in comparison with conventional substances such as hyaluronic acid. Hyaluronic acid, which is the most widely used filler material at this moment in time, lacks bioactivity and therefore does not promote the formation of tissue or achieve lasting improvements over time, which means that it has to be administered on a periodic basis, generally every three to four months.

Example 3

The method starts by extracting a 9 ml blood sample from a patient and storing the blood in a tight-sealed extraction tube that contains 0.1 ml of 3.8% citrate anticoagulant. The blood is centrifuged at a speed of 580 g for 8 minutes and at an ambient temperature. As a result of the centrifuging, the blood contained in the tube is divided into various fractions. The top fraction, or fraction of platelet-rich plasma (PRP), is extracted to a 5 ml syringe without including the white blood cells. Then, 10% calcium chloride is added in a ratio of 50 µl for each 1 ml of plasma, causing the activation of the platelets, i.e. the release of growth factors, and the coagulation of the plasma. The syringe is then heated at a temperature of 75° C. for 5 minutes. The syringe is then cooled at an ambient temperature for 10 minutes. As a result of this thermal heating-cooling sequence, a semi-solid substance forms inside the syringe. The substance has a gel-like consistency as a result of both the fibrin generated due to the coagulation, and the gelation of the proteins produced by the heat treatment. The substance includes citrate, calcium and released growth factors. A substance of this type may be used for filling a bone defect, such as an alveolus left following the extraction of a dental piece, to encourage the regeneration of the alveolus. Thanks to the release of growth factors and the ability of the gel to act as support for cell growth, the gel encourages the filling of the alveolus with bone tissue, thereby cutting waiting times for the further fitting, for example, of a dental implant in the alveolus in replacement of the extracted tooth.

Example 4

The method starts by extracting a 9 ml blood sample from a patient and storing it in a tight-sealed extraction tube containing 0.1 ml of a sodium citrate solution with a concentration of 3.8% (weight/volume), which acts as an anticoagulant. The blood is centrifuged at a speed of 580 g for 8 minutes and at an ambient temperature. As a result of the centrifuging, the blood contained in the tube is divided into various fractions. The top fraction, or fraction of platelet-rich plasma (PRP), is extracted to a 9 ml fractionating tube without the white cells. A calcium chloride solution (with 10% weight/volume concentration) is added at a ratio of 50 µl for each 1 ml of plasma. The tube is then inserted into an oven at 37° C. The calcium chloride causes the activation of the platelets (growth factor release), the coagulation of the plasma and the formation of fibrin, said formation being accelerated by the fact that the tube is submitted to the oven temperature conditions. As a result of the clot retraction, two phases are then obtained: a solid phase, which is a three-dimensional fibrin structure, and a liquid supernatant phase, which contains proteins, platelet growth factors and plasma growth factors. The liquid phase or supernatant is separated into a 3 ml syringe. The syringe is then heated at a temperature of 80° C. for 10 minutes. The syringe is then cooled at a temperature of 22° C. for 5 minutes. As a result of this thermal heating-cooling sequence, a semi-solid substance is formed inside the syringe. This semi-solid substance has a less solid consistency than formulations in accordance with the invention that do comprise fibrin. Due to its less solid consistency, a substance of this type may be useful, for instance, for filling periodontal intra-bone defects for the purpose of promoting the regeneration of periodontal tissue. It may also be useful for regenerating bone by carrying out a subperiosteal or supraperiosteal infiltration of the substance.

Example 5

In another example, the method started with a fibrin clot (a substance prepared after centrifuging blood at a speed of 580 g and a temperature of 20° C. to obtain platelet-rich plasma, adding calcium chloride in a proportion of 50 µl of calcium chloride for each 1 ml of plasma, and waiting for 10 to 20 minutes until the fibrin polymerises). The clot was subjected to heating at 70° C. for 10 minutes, followed by cooling at 20° C. for 10 minutes, with a protein gel thereby being obtained. FIG. 1 shows two electron microscopic images of the aforementioned protein gel. The image on the left shows the presence of rounded structures that represent the denaturalised albumin and linear structures that are fibres of fibrin. The image on the right shows the compact (outer) surface of the gel.

Example 6

In another example, the method started with a plasma rich in growth factors (PRGF) (a substance prepared after centrifuging blood at a speed of 580 g and a temperature of 20° C. to obtain various fractions, separating a fraction of platelet-rich plasma (PRP) and adding calcium chloride in a proportion of 50 µl of calcium chloride for each 1 ml of plasma, for the purpose of causing the release of growth factors and starting the coagulation of the plasma). The retraction of the clot allowed a supernatant to be obtained. Said supernatant was then subjected to heating at 70° C. for 10 minutes, followed by cooling at 20° C. for 10 minutes, with a protein gel being obtained. FIG. 2 shows two electron microscopic images of the aforementioned protein gel. The image on the left shows the interior of the gel and the presence of rounded structures that represent the denaturalised albumin. The image on the right shows the compact (outer) surface of the gel.

Example 7

In another example, various protein gels were prepared by subjecting a fibrin clot (prepared as described in Example 5) at different temperatures and times. The preparation conditions were as follows: heating of the clot at 70° C. for 15 minutes (square), heating of the clot at 70° C. for 30 minutes (circle), heating of the clot at 80° C. for 15 minutes (triangle); and cooling them all at a temperature of 4° C. for 10 minutes. These gels were dried at 37° C. for 24 hours before being incubated in distilled water. The gels were weighed at intervals of 24 hours in order to calculate the degree of swelling, defined as: swollen weight/initial weight. FIG. 3 shows the degree or swelling factor of the protein gels prepared at different temperatures and times. As can be seen, the gels increase between 2 and 3 times their initial weight due to the absorption of water and its retention inside the structure. It can also be seen that the gels prepared at 70° C. for 15 minutes (square) swell in 24 hours and their swelling factor does not significantly change over longer incubation times. However, the gels prepared at 70° C. for 30 minutes (circle) swell to approximately 3 times their initial weight after 24 hours, but as the incubation time increases a slight drop in the swelling factor is observed. Meanwhile, the gels prepared at 80° C. for 15 minutes (triangle) take longer than the two preceding ones to reach maximum swelling, specifically 48 hours. In any case, the swellability of the gels means they can be used, for example, as matrices for the local release of bioactive substances (proteins or main active substances). This use is normally carried out by applying a solution that contains said bioactive substances on the dehydrated gels, which thus causes the gels to hydrate and therefore incorporate the bioactive substances.

Example 8

Figure 4:
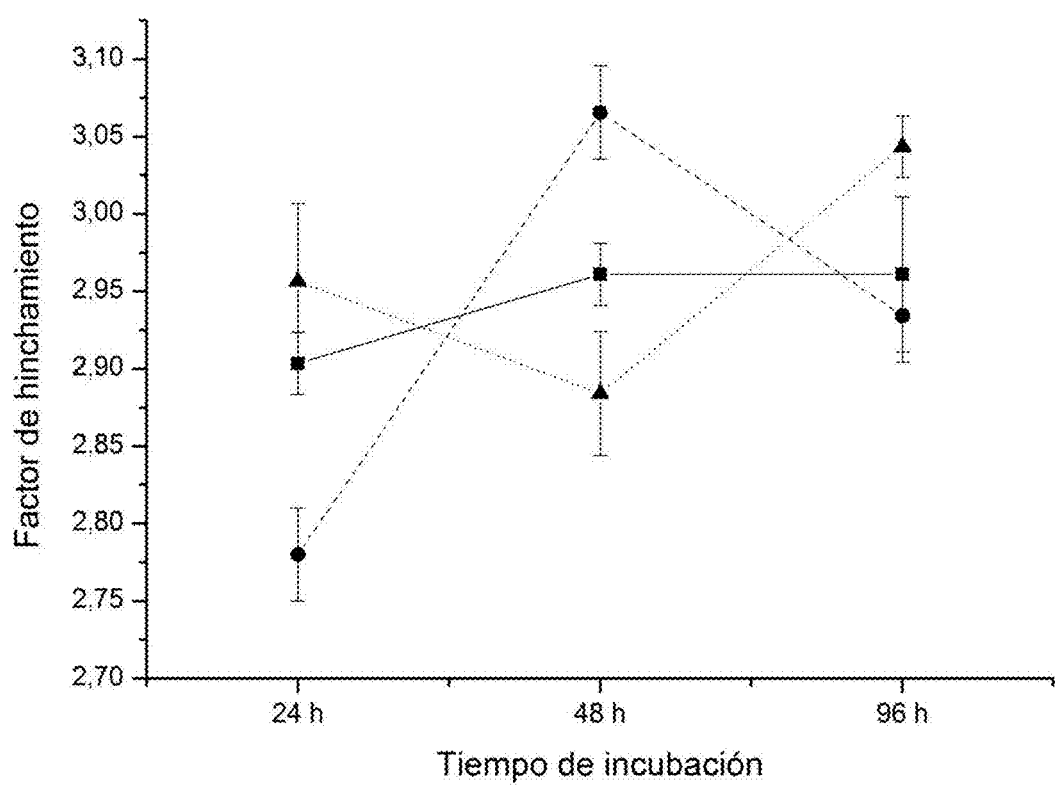
FIG. 4 shows the swelling factor of various formulations in accordance with the invention, prepared by treating a supernatant at different temperatures and times.

In another example, various protein gels were prepared by subjecting a supernatant (prepared according to Example 6) at different temperatures and times. The preparation conditions were as follows: heating of the supernatant at 70° C. for 15 minutes (square), heating of the supernatant at 70° C. for 30 minutes (circle), heating of the supernatant at 80° C. for 15 minutes (triangle); and cooling them all at a temperature of 4° C. for 10 minutes. These gels were dried at 37° C. for 24 hours before being incubated in distilled water. The gels were weighed at intervals of 24 hours in order to calculate the degree of swelling, defined as: swollen weight/initial weight. The initial weight is the weight of the dry gel before its incubation in water. FIG. 4 represents the degree of swelling of the protein gels prepared at different temperatures and times. As can be seen, the initial weight of the gels has increased approximately 3 times due to the absorption of water and the retention of it inside its structure. It can also be seen that the gels prepared at 70° C. for 15 minutes (square) swell in 24 hours and that their swelling factor does not change significantly at longer incubation times. In contrast, the gels prepared at 70° C. for 30 minutes (circle) swell to 3 times their initial weight after 48 hours, but a slight drop in the swelling factor is observed at a longer incubation time. Meanwhile, the gels prepared at 80° C. for 15 minutes (triangle) reach said swelling factor approximately equal to 3 following 24 hours of incubation. In any case, the swellability of the gels allows them to be used, for example, as matrices for locally releasing bioactive substances (proteins or active ingredients). This use is normally carried out by applying a solution that contains said bioactive substances on the dehydrated gels, thus causing the gels to hydrate and therefore incorporate the bioactive substances in their interior.

Example 9

Figure 5:
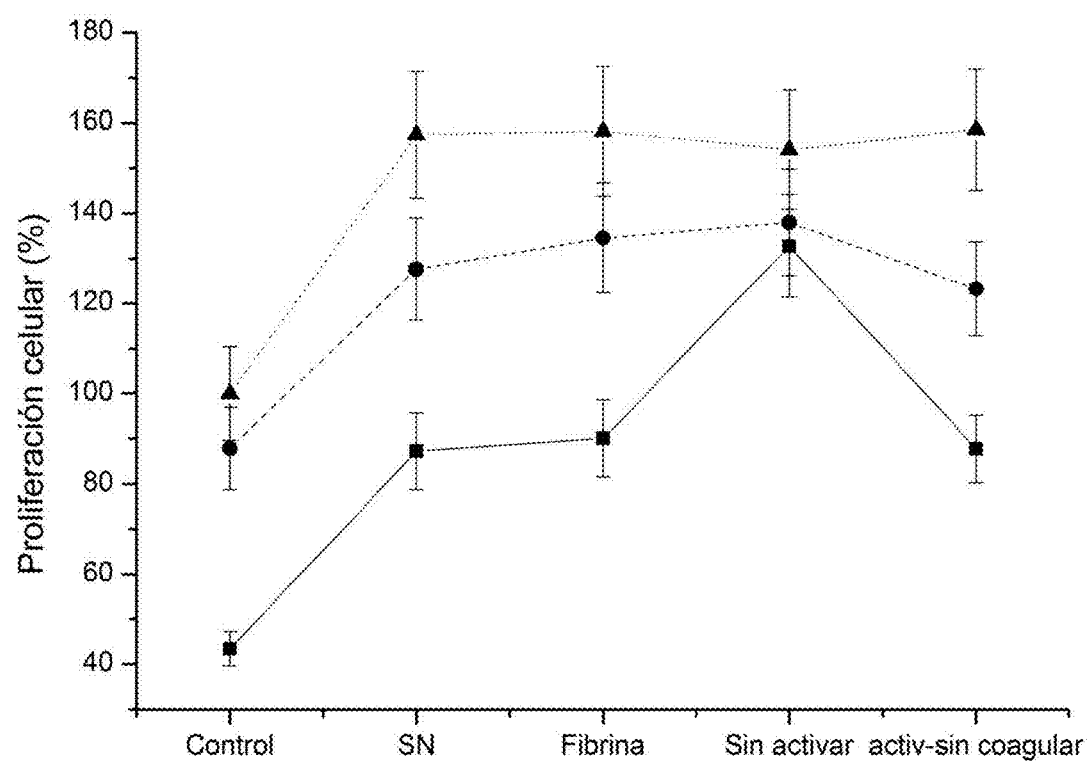
FIG. 5 shows cytocompatibility results of various formulations in accordance with the invention, tested with the MG 63 osteoblast-like cell line.

In another example, four protein gels or formulations were prepared in accordance with the invention from: a supernatant (indicated as "SN" in the graph referred to at the end of this example), a fibrin clot ("Fibrin"), a non-activated platelet-rich plasma ("Non-activated") and a platelet-rich plasma activated with 10% CaCl2 without clotting ("Activated-without clotting"), and carrying out a heat treatment of the aforementioned initial substances consisting in heating the substances at 70° C. for 15 minutes and cooling them at 21° C. for 10 minutes. The methods for preparing these initial substances are explained in Examples 2, 3 and 6. Each of these four formulations obtained following heat treatment was incubated for 48 hours in Dulbecco's Modified Eagle's Medium (DMEM) without fetal bovine serum for 48 hours. In addition, the method also parted with a fifth substance or control substance, consisting of the DMEM without fetal bovine serum. The five culture media were used to cultivate MG 63 cells, being renewed every 2 (square), 4 (circle) and 7 (triangle) days. Following each of these periods of time, cell proliferation was evaluated using the colorimetric reagent WST-1 and a plate reader. The percentage of proliferation was calculated using the following function: % proliferation=(gel absorbance of WST-1/control substance absorbance of WST-1)×100. FIG. 5 shows the cytocompatibility results of protein gels tested with the MG 63 osteoblast-like cell line. As can be seen, the gels are not toxic, as shown by the increase in cell proliferation in relation to the control samples. After two days of proliferation (square) the gel prepared from the non-activated platelet-rich plasma resulted in greater cell proliferation. However, these differences do not arise at longer proliferation times (circle, triangle). This example therefore demonstrates that the formulations in accordance with the invention present suitable behaviour for stimulating cell growth and are biocompatible, allowing them to be developed towards clinical use.

Example 10

Figure 6:
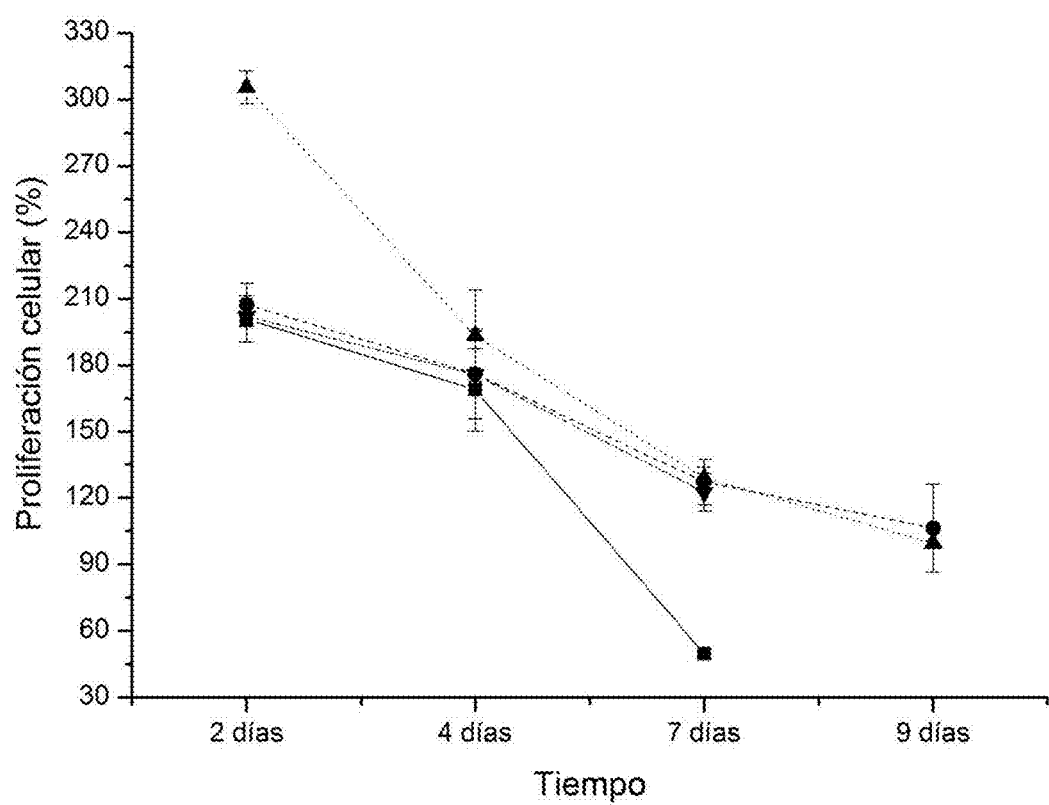
FIG. 6 shows other cytocompatibility results of various formulations in accordance with the invention, tested with the MG 63 osteoblast-like cell line.

As in the preceding example, four protein gels or formulations were prepared in accordance with the invention from: a supernatant (square), a fibrin clot (circle), a non-activated platelet-rich plasma (a triangle with central vertex pointing upwards) and a platelet-rich plasma activated with 10% CaCl2 without clotting (a triangle with central vertex pointing downwards). All substances were subjected to a heat treatment consisting in heating the substances at 70° C. for 15 minutes and cooling them at 21° C. for 10 minutes. The methods for preparing these initial substances are explained in Examples 2, 3 and 6. The four formulations obtained were incubated in a culture medium for 2, 4, 7 and 9 days. At the end of each time period, the media were collected and a new medium added to the gels. The collected media were stored for their use in cultivating the MG 63 cells. The cells were allowed to grow in this medium for 48 hours. Cell proliferation was then evaluated using the colorimetric reagent WST-1 and a plate reader. The percentage of proliferation was calculated using the following function: % proliferation=(gel absorbance of WST-1/control substance absorbance of WST-1)×100, where DMEM without serum was used as the control substance. FIG. 6 shows the cell proliferation in a culture medium and at each incubation time interval. As can be seen, the greater cell proliferation was achieved after 2 days of incubation. At longer incubation times, the culture media promoted less cell proliferation, which seems to suggest that the release of growth factors was greater following 2 days of incubation and that this content in growth factors was smaller than in the media with longer incubation times (4, 7 and 9 days). These results therefore show that the release of cell-proliferation-stimulating substances in the gels decreases over time, following a release profile similar to other types of gels which are characterized in releasing large amounts of bioactive substances during the first few hours of incubation ("burst" effect), and that with the passing of time the released amount decreases significantly.

Example 11

Figure 7:
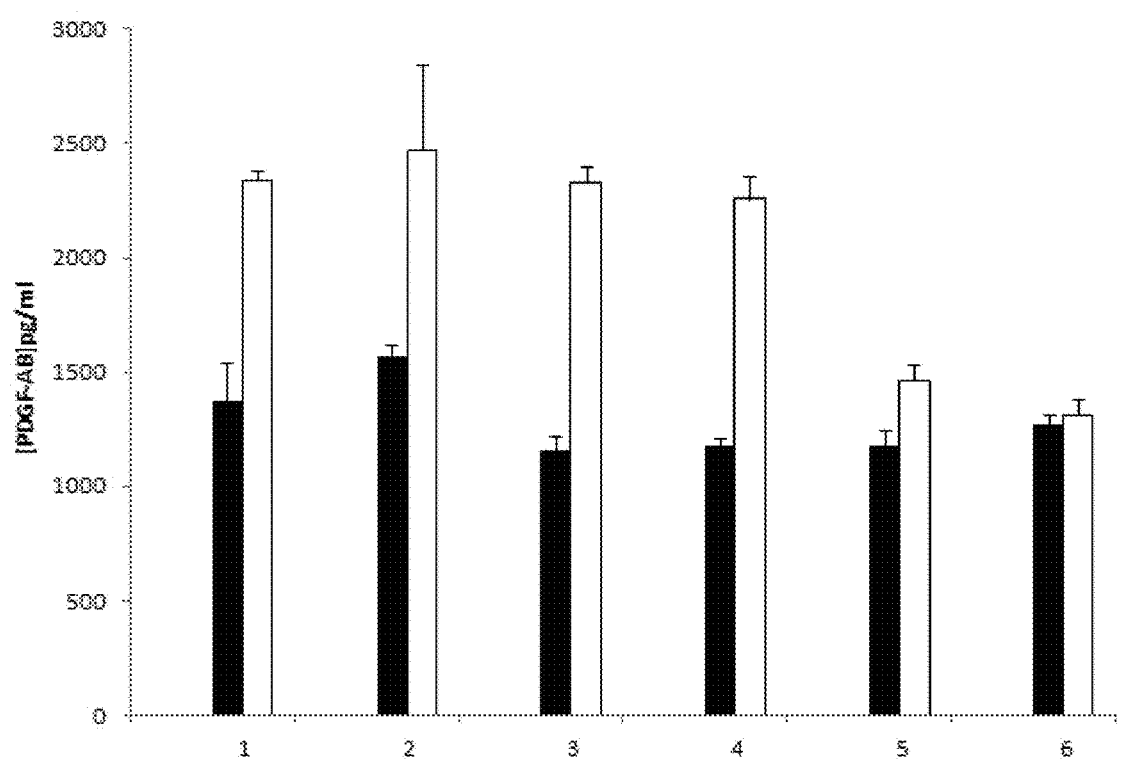
FIGS. 7 and 8 respectively show the content in platelet-derived growth factor (PDGF-AB) and in beta transforming growth factor (TGF-β) in twelve formulations in accordance with the invention.
Figure 8:
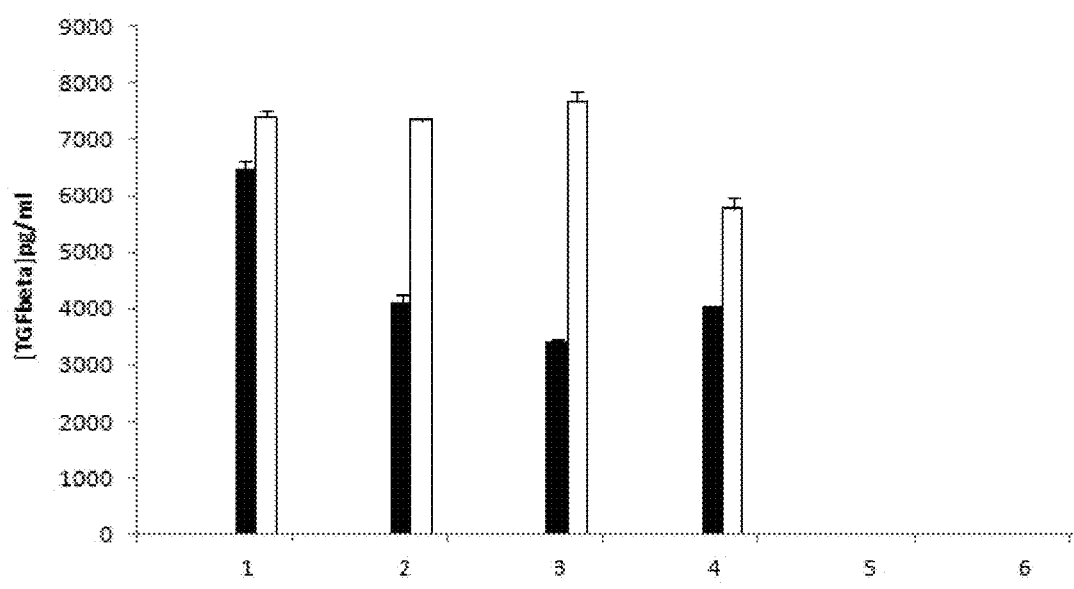

In another example, the method started with two initial substances. The first substance was a fibrin gel obtained after activating a platelet-rich plasma with calcium chloride at a ratio of 50 μl for each 1 ml of plasma (as in Example 6). The second substance was a supernatant obtained following the retraction of a fibrin gel (as in Example 6). Both substances were subjected to three different heat treatments: heating at 70° C. for 15 minutes, heating at 70° C. for 30 minutes and heating at 80° C. for 15 minutes. In all cases, heating was followed by cooling at a temperature of 4° C. or at a temperature of 20° C., for 10 minutes. Twelve protein gels were obtained. The twelve gels were then centrifuged at 14,800 rpm for 20 minutes. The content of platelet-derived growth factor (PDGF-AB) and beta transforming growth factor (TGF-β) was then measured. The results of these measurements are shown in FIGS. 7 and 8, where the twelve gels are shown in six groups of two, the groups being named "1" (fibrin gel at 70° C., 15 minutes), "2" (fibrin gel at 70° C., 30 minutes), "3" (fibrin gel at 80° C., 15 minutes), "4" (supernatant gel at 70° C., 15 minutes), "5" (supernatant gel at 70° C., 30 minutes) and "6" (gel of supernatant a 80° C., 15 minutes), and where, in each group, the gel cooled at 4° C. is indicated with a black bar and the gel cooled at 20° C. with a white bar. FIG. 7 shows the content of PDGF-AB growth factor observed. It can be concluded that the content of this growth factor was generally greater in the gels cooled at 20° C. (white bars) than in the gels cooled at 4° C. (black bars), with the exception of the supernatant gels prepared at 70° C. for 30 minutes ("5") and at 80° C. ("6"), where hardly any differences were observed in the content of PDGF-AB in dependence of the cooling temperature. FIG. 8 shows the observed contents of the TGF-β growth factor. It can be concluded that, with regard to the gels prepared from fibrin (groups "1", "2", "3"), in the case of cooling carried out at 20° C. (white bars) the content of the TGF-β factor was similar in the three groups, i.e. for different heat treatments for preparing gels, while in the case of cooling carried out at 4° C. (black bars) the content of the TGF-β factor was greater in the gel prepared at 70° C. for 15 minutes (group "1"). In contrast, with regard to the gels prepared from the supernatant (groups "4", "5", "6"), it can be seen that only the protein gel prepared from supernatant at 70° C. for 15 minutes (group "1") released TGF-β, with said factor not being detected in the other gels prepared from the supernatant. It may thus be concluded that the fibrin gel maintains a higher growth-factor content than the supernatant at temperatures in excess of 70° C. and that the heating temperature and the cooling temperature therefore affect this growth-factor content, the content being greater at lower heating temperatures and at a cooling temperature of 21° C. It may also be concluded that PDGF-AB is more stable than TGF-β at high temperatures and that protein gel based on fibrin contains a larger quantity of TGF-β than the protein gel based on the supernatant.

Example 12

Figure 9:
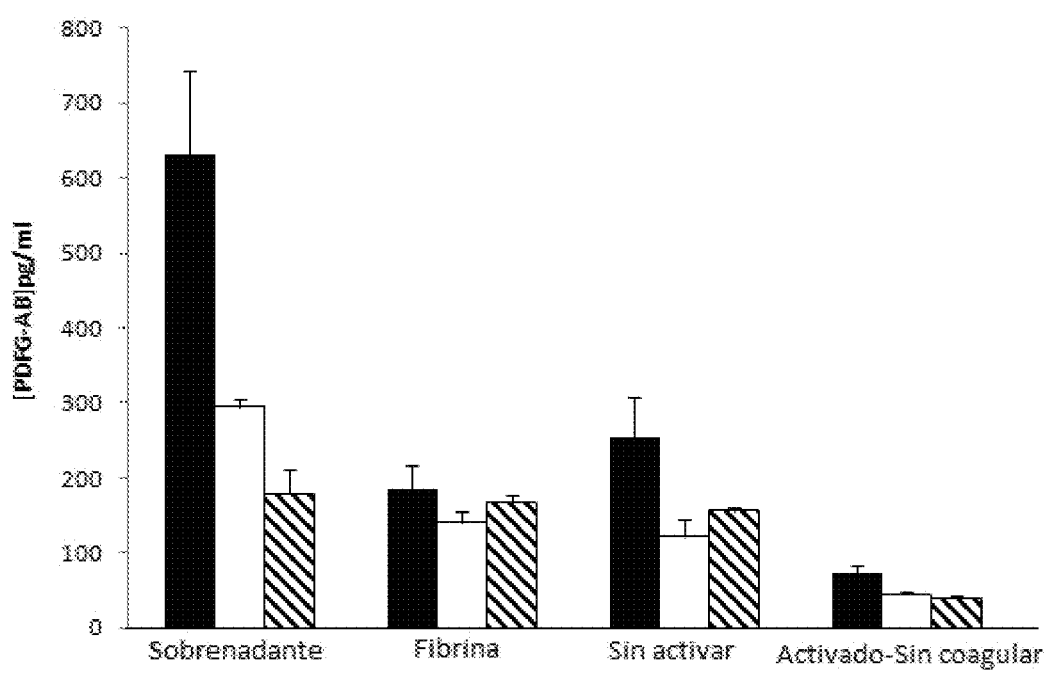
FIG. 9 shows the release kinetics of the PDGF-AB growth factor in four inventive formulations incubated for different periods of time.
Figure 10:
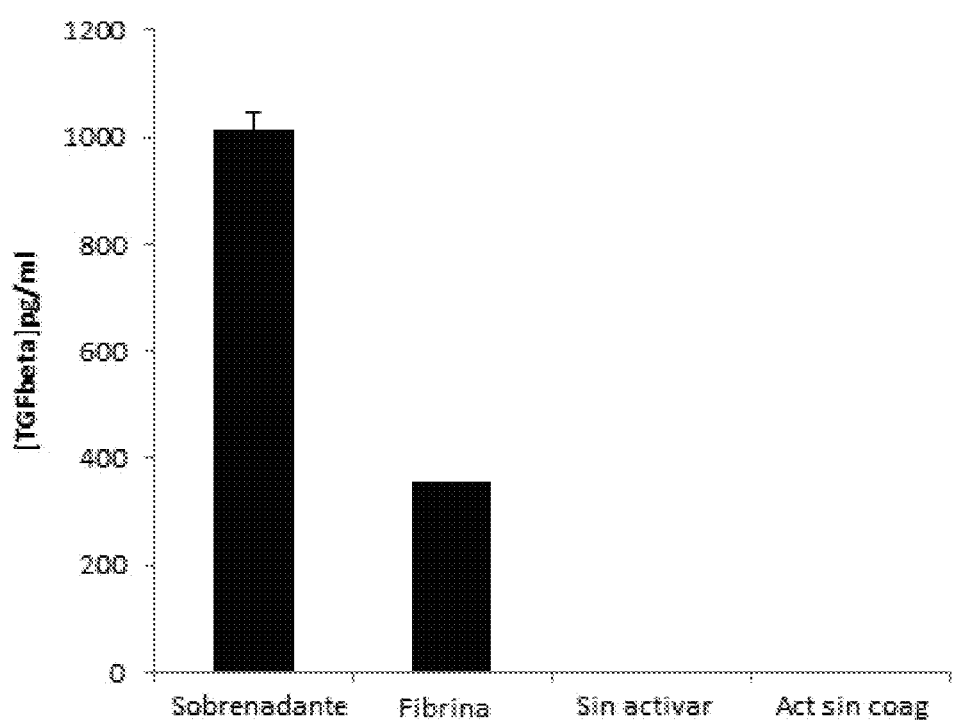
FIG. 10 shows the release kinetics of the TGF-β growth factor in four formulations in accordance with the invention, when incubated for two days.

In another example, four protein gels or formulations were prepared in accordance with the invention, by applying a heat treatment that consisted in heating the following initial substances at 70° C. for 15 minutes and cooling them at 21° C. for ten minutes: a supernatant (SN), a fibrin clot (fibrin), a non-activated platelet-rich plasma (not activated) and a platelet-rich plasma activated with 10% CaCl$_2$ without clotting (activated without clotting). The preparation of these initial substances is explained in Examples 2, 3 and 6. The four protein gels were incubated in DMEM for different periods of time (2, 4 and 7 days). At each incubation time, the media time were extracted to determine the content of PDGF-AB and TGF-β with the objective of determining the release kinetics of these growth factors of the four protein gels. FIG. 9 shows the release kinetics of PDGF-AB in a DMEM medium, with the measurements corresponding to the incubation time periods of 2, 4 and 7 days being indicated with black, white and striped bars. It can be seen that the release of PDGF-AB was greater during 2 and 4 days of incubation for the protein gel prepared from the supernatant. The other gels do not reveal any significant differences between the three incubation times. In turn, FIG. 10 shows the release kinetics of TGF-β in a DMEM medium after 2 days of incubation. It can be seen that this factor was present only in the protein gels prepared from the supernatant and the fibrin, the release of TGF-β in the protein gel from the supernatant being greater. It may be concluded, therefore, that growth factors are released more quickly from protein gels based on the supernatant.

Example 13

Figure 11:
FIG. 11 shows a photograph of the back of a laboratory rat into which samples of four formulations in accordance with the invention have been injected.

In another example, the filling effect of proteins gels or formulations in accordance with the invention was tested on laboratory rats. Four inventive formulations were prepared for this purpose. The preparation of the four formulations began with the following steps. Firstly, blood was extracted from patients to 9 ml tubes without anticoagulant. The tubes were centrifuged at 850 g for 8 minutes to separate the plasma from the red blood cells. The entire column of plasma situated above the fraction of red blood cells, excluding the leukocytes, was then extracted to new 9 ml tubes. This plasma was used to prepare the following: the plasma liquid itself (B); a fibrin clot (C), for the purposes of which 10% calcium chloride was added in a ratio of 50 µl for each 1 ml of plasma, causing the activation of the plasma and the formation of the clot; and a supernatant (A), for the purposes of which a fibrin clot with the same characteristics as the aforementioned one was prepared, and a period of 60 minutes at 37° C. was allowed to lapse, enabling the fibrin to retract and the supernatant to be obtained. Blood was also extracted from the patients in 9 ml extraction tubes with 0.1 ml of 3.8% of sodium citrate as an anticoagulant. The blood was centrifuged at 850 g for eight minutes, with 2 ml of plasma just above the leukocyte-platelet layer being obtained and activated with 10% calcium chloride in a ratio of 50 µl for each 1 ml of plasma to obtain the fibrin clot (D). These four initial substances (A, B, C, D) were treated at 70° C. for 10 minutes and cooled at 20° C. for 10 minutes to obtain the gels. A dose of 0.6 ml of each of the gel formulations was administered to each rat. The photograph shown in FIG. 11 shows the formation of an increase in volume sustained by the protein gels, indicating an improvement in their mechanical properties.

In addition a plasma rich in growth factors (which will be referred to as "PRGF-Endoret") was prepared by extracting blood in 9 ml tubes with 0.1 ml of 3.8% of sodium citrate, centrifuging the blood at 850 g for eight minutes, separating the fraction of plasma rich in platelets (the 2 ml of the plasma column just above the fraction of red blood cells, without including the leukocytes) and, at the moment prior to injecting in the rat, activating the plasma (causing the release of growth factors of the platelets) by adding 50 µl of calcium chloride for each 1 ml.

Figure 12:
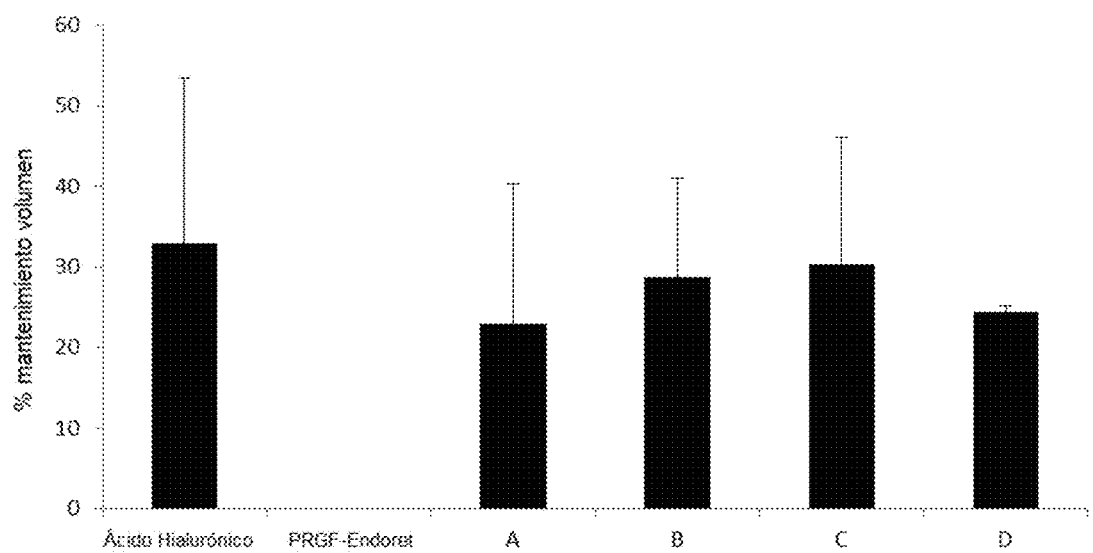
FIG. 12 shows a graph related to the test of the previous figure, showing the volume of the hemiellipse after injecting the formulations at an intradermal level, measured two weeks after the injection.

FIG. 12 shows the changes in volume after 2 weeks of injecting the protein gels in rats and using hyaluronic acid and the PRGF-Endoret plasma rich in growth factors described above as controls. It may be concluded that the protein gels were as effective in maintaining the volume of the hemiellipse as hyaluronic acid, while the PRGF-Endoret plasma rich in growth factors was not useful in maintaining the volume of the hemiellipse.

It should be added that, during the test, an attempt was also made to inject conventional fibrin gel (clot), for the purpose of comparing the stability of the protein gels according to the invention with the stability of the fibrin gel. The result was that it was not possible to inject said fibrin gel because a phase separation occurred (with the fibrin separating from the supernatant), preventing the fibrin gel from being administered as such.

Example 14

The platelet-rich plasma is prepared as described in Example 2. Type-I collagen is then added. The mixture is then heated at a temperature of 75° C. for 10 minutes and subsequently cooled at a temperature of 20° C. for 3 minutes. The result of this preparation is a protein gel that shows greater consistency. This type of gel may be used as filler for treating wrinkles as it shows greater stability and a slower rate of degradation than without the collagen. This modification thus helps slow down the degradation of the formulation even further. Clinically, this improvement in stability increases the period between a first and second administration of the gel. This represents a solution to the drawback of the treatment of wrinkles with hyaluronic acid, which involves repeating its administration every 3 to 4 months, in other words, in a short period of time.

Example 15

The platelet-rich plasma is prepared as described in Example 2. Calcium phosphate, for instance in granular form, is then added. The mixture is then heated at a temperature of 80° C. for 10 minutes and is cooled at a temperature of 20° C. for 3 minutes. The hybrid material resulting from this preparation shows better mechanical properties than the gel that has not been modified with calcium phosphate. The modification of gel with calcium phosphate increases the gel's resistance to compression and tension forces. This type of material may be used to regenerate bone defects that require the filler material to have greater mechanical stability because of the lack of one or more walls in the defect.

Example 16

The protein gel in accordance with the invention is prepared, using a method of preparation described in any of the aforementioned examples. The gel is then combined with hyaluronic acid to produce a hybrid material. This material shows better viscoelastic properties, which enhances its stability in the area of administration, thereby preventing its migration. This hybrid material is useful for its application on surfaces such as the vestibular wall of the narrow alveolar process to cause a horizontal bone growth and thereby increase the thickness of the alveolar process to enable the insertion of dental implants with sufficient bone covering.

Example 17

After preparing and drying the gel as described in Example 8 (any of the examples of protein gel described therein is valid), the dry material is incubated, for 24 hours and in darkness, in a liquid that contains a doxycycline hyclate antibiotic in a concentration of 15 mg/ml. The result is the swelling of the gel, the gel's structure including the antibiotic for its subsequent release in the area of application. This gel can now thus be used for the controlled release of the antibiotic for the treatment of an infection in an area where there is a lower blood supply—the bone, for example—and prevents the systemic administration of the antibiotic. This procedure may be repeated with other antibiotics and other medicines to guarantee their local release.

The invention claimed is:

1. A method for preparing a gelled human blood composition rich in released growth factors and platelets consisting essentially of:
    a) mixing an initial human blood composition rich in platelets and/or growth factors with hyaluronic acid and sodium citrate to form a mix;
    b) heating the mix to a temperature of between 70° C. and 85° C. for at least 1 minute;
    c) cooling the heated mix to a temperature of between 4° C. and 20° C. for at least 1 minute to yield a gelled human blood composition rich in released growth factors and platelets.

2. The method of claim 1, wherein the initial human blood composition is a platelet-rich blood plasma.

3. The method of claim 1, wherein the initial human blood composition is a supernatant of a platelet-rich blood plasma.

4. The method of claim 1, wherein the initial human blood composition is a blood plasma that is rich in released growth factors.

5. The method of claim 1, wherein the initial human blood composition is a supernatant of a blood plasma that is rich in released growth factors.

6. The method of claim 1, wherein the initial human blood composition is also a fibrin gel.

7. The method of claim 1, wherein, prior to heating, a step of activating the platelets and waiting until formation of a provisional fibrin is performed.

* * * * *